US00PP32723P2

(12) United States Plant Patent
White

(10) Patent No.: US PP32,723 P2
(45) Date of Patent: Jan. 5, 2021

(54) ***BETULA* TREE NAMED 'STN-01'**

(50) Latin Name: *Betula nigra*
Varietal Denomination: STN-01

(71) Applicant: Ronald Lee White, McAlpin, FL (US)

(72) Inventor: Ronald Lee White, McAlpin, FL (US)

(73) Assignee: Shade Tree Nursery, McAlpin, FL (US)

( * ) Notice: Subject to any disclaimer, the term of this patent is extended or adjusted under 35 U.S.C. 154(b) by 0 days.

(21) Appl. No.: 16/873,454

(22) Filed: Apr. 15, 2020

(51) Int. Cl.
*A01H 5/04* (2018.01)
*A01H 6/00* (2018.01)

(52) U.S. Cl.
USPC ..... Plt./216

(58) Field of Classification Search
USPC ..... Plt./216
CPC ..... A01H 5/00; A01H 5/04; A01H 6/00
See application file for complete search history.

*Primary Examiner* — June Hwu
(74) *Attorney, Agent, or Firm* — Samuel R. McCoy, Jr.

(57) ABSTRACT

A new and distinct *Betula nigra* tree named 'STN-01' which is characterized by a significantly shorter tree height, a freely branching and densely foliaged growth habit, main stems and lateral branches with shortened internodal spacing, relatively large and dark green foliage, and prominent bark exfoliation of the oldest wood. The claimed plant propagates successfully by softwood stem cuttings and has proven to be uniform and stable in the resulting generations.

3 Drawing Sheets

Latin name of the genus and species: The Latin name of the genus and species of the novel variety disclosed herein is *Betula nigra.*

Variety denomination: The inventive variety of *Betula nigra* disclosed herein has been given the variety denomination 'STN-01'.

BACKGROUND OF THE INVENTION

Parentage: The claimed tree is a seedling selection of unknown parentage which was discovered at a commercial tree nursery in McAlpin, Fla. In the spring of 2004, the claimed plant was discovered growing amongst a population of openly-pollinated, unnamed *Betula nigra* trees (not patented) which were in cultivation in 20 gallon nursery containers. Said tree exhibited a dwarfed and densely foliaged growth habit when compared to other *Betula nigra* progeny in the population and other specimens that typify the species. The tree was isolated and grown for an additional year to confirm the distinctness and stability of the characteristics initially observed. Upon further evaluation and confirmation of the desirable traits, the claimed tree was selected for commercialization.

Asexual Reproduction: In 2005, 'STN-01' was first asexually reproduced by way of softwood stem cuttings in McAlpin, Fla. The claimed tree was found to asexually reproduce in uniform and stable manner and 10 successive cycles of vegetative propagation have proven to be true to type.

SUMMARY OF THE INVENTION

The following characteristics have been repeatedly observed and represent the distinguishing characteristics of the new *Betula nigra* tree, 'STN-01'. These traits, in combination, distinguish 'STN-01' as a new and distinct cultivar.

1. 'STN-01' exhibits a significantly shorter tree height with a freely branching and densely foliaged growth habit; and
2. 'STN-01' exhibits main stems and lateral branches with shortened nodal spacing; and
3. 'STN-01' exhibits relatively large, dark green foliage; and
4. 'STN-01' exhibits prominent bark exfoliation.

BOTANICAL DESCRIPTION OF THE PLANT

Figure 1:
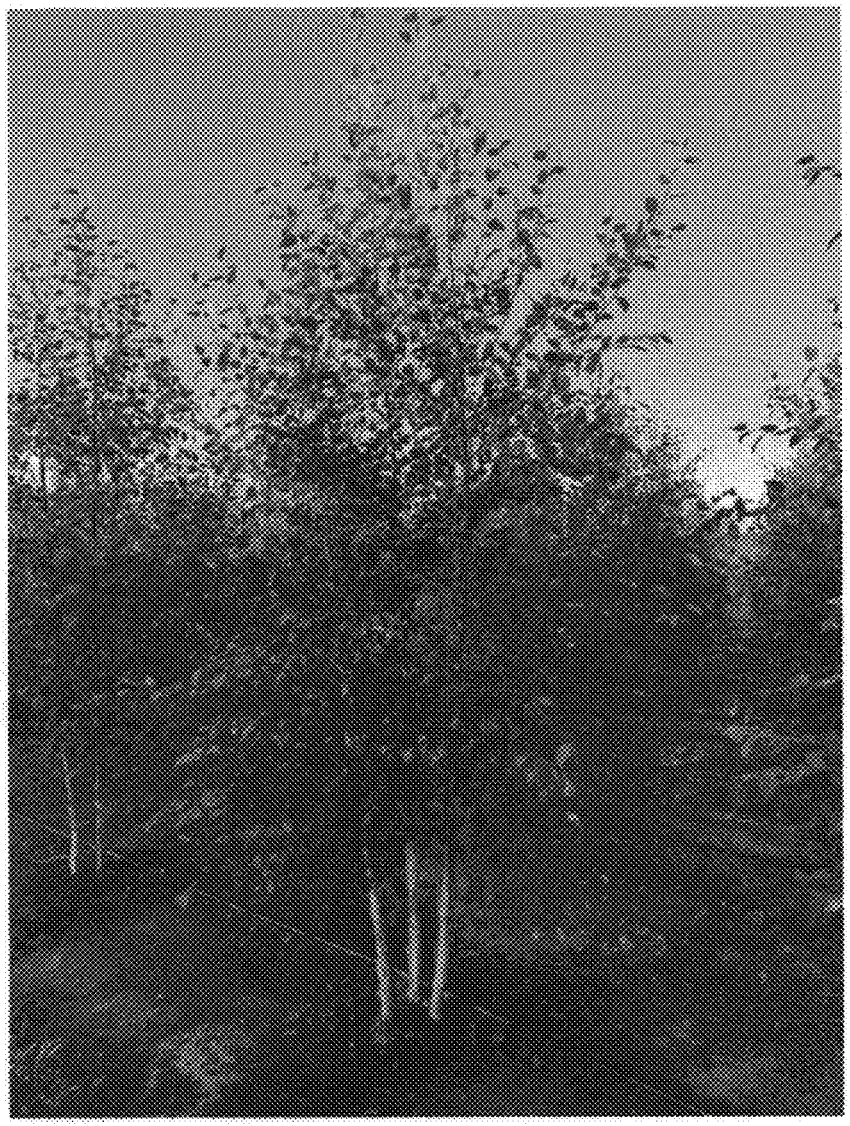
FIG. 1 illustrates, as nearly true as it is reasonably possible to make the same in color photographs of this type, a field-grown 'STN-01' tree at approximately 7 years of age, during spring in McAlpin, Fla.
Figure 2:
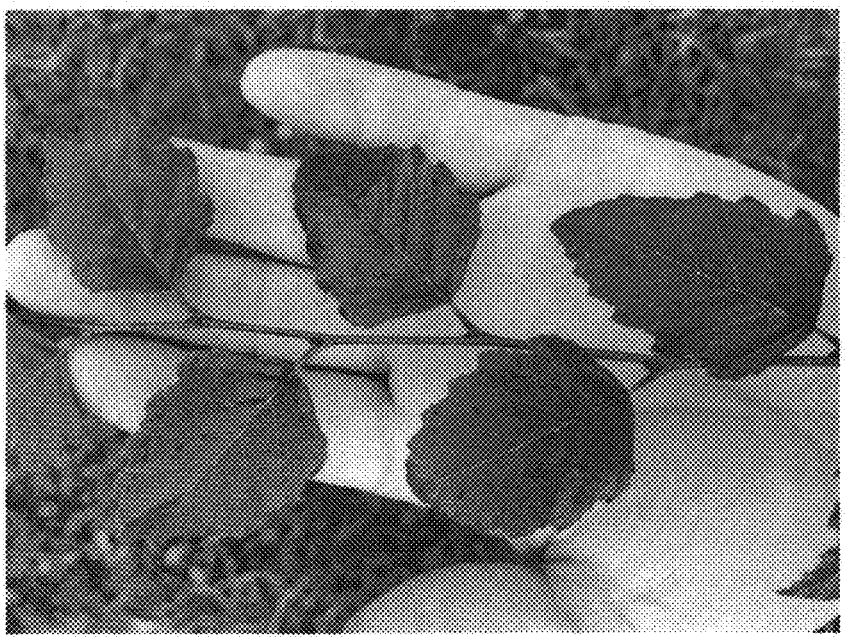
FIG. 2 illustrates, as nearly true as it is reasonably possible to make the same in color photographs of this type, the exemplary mature foliage of 'STN-01'.
Figure 3:
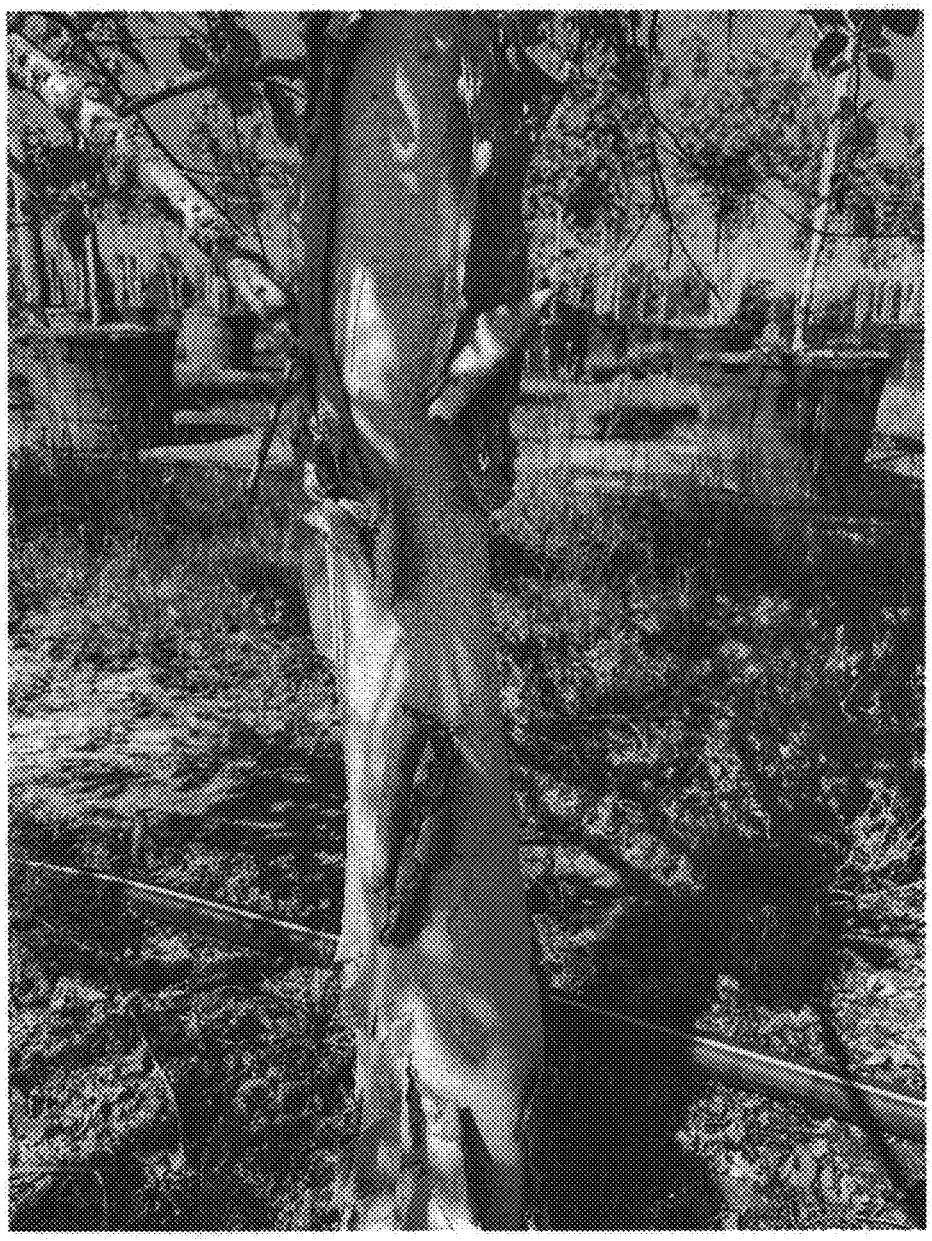
FIG. 3 illustrates, as nearly true as it is reasonably possible to make the same in color photographs of this type, the oldest wood of a field-grown 'STN-01' tree at approximately 7 years of age, during spring in McAlpin, Fla. Of note is the high degree of bark exfoliation.

The following is a detailed botanical description of a new and distinct *Betula nigra* plant cultivar known as 'STN-01'. Plant observations were made on a field-grown 7 year-old tree in McAlpin, Fla. The observed tree was grown in full exposure to natural sunlight, and maintained with drip irrigation. No pest or pathogen countermeasures were employed. Observation data was recorded in April of 2020.

Those skilled in the art will appreciate that certain characteristics will vary with older or, conversely, younger plants. 'STN-01' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition except where common terms of color are used.

A botanical description of 'STN-01' and comparisons with the presumed parent and most similar commercial cultivar are provided below.

General plant description:

*Plant habit*.—Monoecious deciduous tree with an upright ascending, freely branching growth habit.

*Tree crown profile*.—Pyramidal and maturing to rotund, when cultivated as a single trunk; when cultivated as a multi-trunked tree, the profile is irregularly rotund.

*Dimensions*.—The original tree grew to approximately 7.5 to 8.0 meters tall and 3.0 to 3.5 meters wide.

*Environmental tolerances*.—Hardy in US Hardiness Zones 5 through 9; prefers cooler climates with moist, loamy soils and full to filtered sun exposure but will tolerate hotter, dryer conditions.

*Pest and disease susceptibility or resistance*.—Plants have not been observed to be susceptible or resistant to pathogens and pests common to *Betula nigra*.

*Propagation*.—Propagation is accomplished using softwood stem cuttings.

*Crop time*.—Approximately one growing seasons are needed to produce a fully rooted 2 gallon nursery container that is ready for transplant into larger nursery containers or directly into the ground for field production.

Root system:

*Description*.—A network of fibrous, non-fleshy roots.

*Rooting habit*.—Freely branching, moderately dense, and relatively shallow in the soil profile.

Stems:

*Branching habit*.—A dominant, near-vertical central main stem, typically unbranched, gives rise to an abundance of lateral branches, themselves freely branching. 'STN-01' can be cultivated as a multi-trunked tree through human intervention. Main stem; central leader — Quantity — One; occasionally branching. Attitude — Erect; near vertical. Aspect — Generally rounded. Diameter — 6.0 to 8.0 cm, at the base of the trunk. Strength — Very strong. Texture — Smooth and becoming progressively fissured and furrowed with age, followed by exfoliation of the bark in large thin, papery sheets, revealing a smooth surface beneath. Exfoliation is most prevalent towards the base of the main stem. Exfoliated sections of bark are clinging and become progressively curled inward from the margins. Color, juvenile — Nearest to a mixture of greyed-orange, RHS 166A, and yellow-green, RHS 152A. Color, mature — Newly exfoliated wood is greyed-orange, RHS 164D and fades to orange-white, nearest to in between RHS 159B and 159C, and ultimately to greyed-green, nearest to in between RHS 196A and 197D. Portions of sloughed off bark, outer surface — Irregularly blotched with varying shades of greyed-green RHS 197A, 197B, 197C, 196B and 196C. Moderately suffused with a mixture of green, RHS 144A, and yellow-green, RHS 146D. Fissures are nearest to a mixture of grey, RHS 201A, and brown, 200C. Portions of sloughed off bark, inner surface — Greyed-orange, RHS 164D and fades to greyed-green, nearest to in between RHS 196A and 197D. Lateral branches — Branch angle to main axis — In between 60 and 70 degrees. Aspect — Round. Diameter — 7.0 mm at the base. Color, juvenile — Yellow-green, nearest to in between RHS 146A and 147C. Color, mature — Nearest to a mixture of greyed-orange, RHS 166A, and yellow-green, RHS 152A. Texture and luster, juvenile — Moderately pubescent and matte. Texture and luster, mature — Glabrous, moderately glossy, and moderately lenticellate. Lenticels are irregularly elliptical to elliptical and range in size from 0.25 mm to 1.0 mm long and 0.25 to 0.5 mm wide; color is greyed-green, nearest to in between RHS 197D and 198D. Stem strength — Strong.

Foliage:

*Arrangement*.—Alternate.

*Attachment*.—Petiolate.

*Division*.—Simple.

*Shape*.—Rhomboid to ovate.

*Length*.—77 mm.

*Width*.—44 mm.

*Apex*.—Acute.

*Base*.—Obtuse.

*Margin*.—Doubly serrate; occasionally slightly undulated.

*Aspect*.—Flat to longitudinally concave; occasionally with a slight axial twist and occasionally reflexed.

*Texture and pubescence, adaxial surface*.—Glabrous, and glossy.

*Texture and pubescence, abaxial surface*.—Pubescent and matte. Juvenile foliage, adaxial surface — Yellow-green, nearest to in between RHS 148A and 148B. Juvenile foliage, abaxial surface — Yellow-green, nearest to in between RHS 148B and 148C. Mature foliage, adaxial surface — Yellow-green, RHS 148A. Mature foliage, abaxial surface — Yellow-green, nearest to in between RHS 146B and 146C.

*Venation*.—Pattern — Pinnate. Vein color, adaxial surface — Yellow-green, nearest to RHS 146D. Vein color, abaxial surface — Yellow-green, nearest to RHS 146D.

*Petiole*.—Length — 10.0 to 12.0 mm. Diameter — 1.5 to 2.0 mm. Color — Yellow-green, nearest to a mixture of RHS 146D. Texture, adaxial and abaxial surfaces — Moderately pubescent.

*Stipules*.—Absent.

Inflorescence: To date, no flowering has been observed on the mother plant or any progeny therefrom.

Flower bud: To date, no flowering has been observed on the mother plant or any progeny therefrom.

Flower: To date, no flowering has been observed on the mother plant or any progeny therefrom.

Reproductive organs: To date, no flowering has been observed on the mother plant or any progeny therefrom.

Fruit and seed: To date, no fruiting has been observed on the mother plant or any progeny therefrom.

COMPARISON WITH THE PRESUMED PARENT PLANT

Plants of the new cultivar 'STN-01' differ from the parent, an unnamed *Betula nigra* tree (not patented), by the characteristics described in Table 1. The pollen parent is presumed to also be an unnamed *Betula nigra* tree (not patented), and therefore no additional comparison to the pollen parent is disclosed.

TABLE 1

| Characteristic | 'STN-01' | The parent |
|---|---|---|
| Tree height. | Significantly shorter than the parent; approximately 50 percent shorter. | Much taller than 'STN-01'. |
| Internode spacing. | Significantly shorter. | Significantly longer. |
| Abundance of foliage. | More abundant. | Less abundant. |
| Foliage size. | Larger and broader than the parent. | Smaller than 'STN-01'. |
| General coloration of the foliage, | Darker shade of green relative to the parent. | Lighter shade of green compared to 'STN-01'. |
| Exfoliation of the older wood. | More pronounced relative to the parent. | Less pronounced compared to 'STN-01'. |

COMPARISON WITH THE MOST SIMILAR *BETULA NIGRA* CULTIVAR KNOWN TO THE INVENTOR

Plants of the new cultivar 'STN-01' are most similar to the commercial cultivar, *Betula nigra* 'BMNTF' (not patented). A comparison of 'STN-01' with *Betula nigra* 'BMNTF' is described in Table 2.

TABLE 2

| Characteristic | 'STN-01' | 'BMNTF' |
|---|---|---|
| Internode spacing. | Significantly shorter. | Significantly longer. |
| Foliage shape. | Broader than 'BMNTF'. | Narrower than 'STN-01'. |
| General coloration of the foliage, | Darker shade of green relative to 'BMNTF'. | Lighter shade of green compared to 'STN-01'. |
| Exfoliation of the older wood. | More pronounced relative to 'BMNTF'. | Less pronounced compared to 'STN-01'. |

That which is claimed is:

1. A new and distinct variety of *Betula nigra* tree named 'STN-01', substantially as described and illustrated herein.

* * * * *